United States Patent [19]

Flick et al.

[11] Patent Number: 5,557,004
[45] Date of Patent: Sep. 17, 1996

[54] PROCESS FOR PRODUCTION OF ALIPHATIC α,ω-AMINONITRILES

[75] Inventors: Klemens Flick, Herxheim; Klaus Ebel, Lampertheim; Werner Schnurr, Herxheim; Johann-Peter Melder, Mannheim; Wolfgang Harder, Weinheim, all of Germany

[73] Assignee: BASF Aktiengesellschaft, Ludwigshafen, Germany

[21] Appl. No.: 370,607

[22] Filed: Jan. 10, 1995

[30] Foreign Application Priority Data

Dec. 27, 1994 [DE] Germany .................. 44 46 895.4

[51] Int. Cl.$^6$ .................................... C07C 255/03
[52] U.S. Cl. .................................... 558/459
[58] Field of Search ............................... 558/459

[56] References Cited

U.S. PATENT DOCUMENTS

| | | | |
|---|---|---|---|
| 2,208,598 | 7/1940 | Rigby | 558/459 |
| 2,257,814 | 10/1941 | Rigby | 558/459 |
| 2,762,835 | 9/1956 | Swerdloff | 558/459 |

FOREIGN PATENT DOCUMENTS

| | | |
|---|---|---|
| 0161419 | 11/1985 | European Pat. Off. |
| WO92/21650 | 12/1992 | WIPO. |
| WO93/12073 | 6/1993 | WIPO. |
| WO93/16034 | 8/1993 | WIPO. |

*Primary Examiner*—Johann Richter
*Assistant Examiner*—John D. Peabody
*Attorney, Agent, or Firm*—Keil & Weinkauf

[57] ABSTRACT

Aliphatic α,ω-aminonitriles are prepared by partial hydrogenation of aliphatic α,ω-dinitriles at elevated temperatures and superatmospheric pressure in the presence of a solvent and of a catalyst, by a process in which the catalyst used is obtainable by thermal decomposition of a metal compound selected from the group consisting of metal carbonyl compounds, metal salts of $C_1$–$C_6$-carboxylic acids and $C_2$–$C_6$-dicarboxylic acids and metal complexes with diketones to give the corresponding metal and/or a metal oxide thereof, with the proviso that the metal used is nickel or cobalt.

5 Claims, No Drawings

PROCESS FOR PRODUCTION OF ALIPHATIC α,ω-AMINONITRILES

The present invention relates to an improved process for the preparation of aliphatic α,ω-aminonitriles by partial hydrogenation of aliphatic α,ω-dinitriles at elevated temperatures and superatmospheric pressure in the presence of a solvent and of a catalyst.

WO 92/21650 describes the partial hydrogenation of adiponitrile to 6-aminocapronitrile in the presence of a Raney nickel catalyst and ammonia as a solvent with a yield of 60% at a conversion of 70%. 9% of hexamethylenediamine are formed as a byproduct. When methanol is used as the solvent and a base other than ammonia is added, the selectivity can be increased to 89.5% at a conversion of 70%. The disadvantage of this process is the short life of the catalyst.

U.S. Pat. Nos. 2,257,814 and 2,208,598 likewise describe preparation processes for 6-aminocapronitrile starting from adiponitrile, the catalysts used being Raney cobalt and iron, nickel and cobalt catalysts on various carriers. The selectivities of from 50 to 60%, which are too low for industrial applications, are a disadvantage of these processes.

In the process of WO 93/16034, the yield of aminocapronitrile can be increased by hydrogenating adiponitrile in the presence of Raney nickel, of a base, such as sodium hydroxide, potassium hydroxide, lithium hydroxide or ammonium hydroxide, and of a transition metal complex with, for example, iron, cobalt, chromium or tungsten as transition metals, and of a solvent. In this process, quantitative yields of aminocapronitrile are described at conversions of from 45 to 60%. The disadvantage of this process is the working up of the generally toxic transition metal complexes from the resulting reaction mixtures.

EP-A 161,419 describes the partial hydrogenation of adiponitrile using a rhodium-containing catalyst on a magnesium oxide carrier in the presence of ammonia. At a conversion of 70%, a selectivity of 94% is achieved. The expensive preparation method for the Rh/MgO catalysts is disadvantageous (cf. J. of Cat. 112 (1988), 145–156).

It is an object of the present invention to provide an improved process for the preparation of aliphatic α,ω-aminonitriles by partial hydrogenation of adiponitrile, which does not have the abovementioned disadvantages; in particular, it was intended to find a process in which the catalysts used have a longer life compared with those of the prior art.

We have found that this object is achieved by a process for the preparation of aliphatic α,ω-aminonitriles by partial hydrogenation of aliphatic α,ω-dinitriles at elevated temperatures and superatmospheric pressure in the presence of a solvent and a catalyst, which comprises using a catalyst which is obtainable by thermal decomposition of a metal compound selected from the group consisting of metal carbonyl compounds, metal salts of $C_1$–$C_6$-carboxylic acids and $C_2$–$C_6$-dicarboxylic acids and metal complexes with diketones to give the metal and/or a metal oxide thereof, with the proviso that the metal used is nickel or cobalt.

We have also found the use of catalysts prepared by thermal decomposition for the partial hydrogenation of α,ω-dinitriles.

Among the metal compounds suitable according to the invention, ie. metal carbonyl compounds, metal salts of $C_1$–$C_6$-carboxylic acids and $C_2$–$C_6$-dicarboxylic acids and metal complexes with diketones, preferably 1,2- and 1,3-diketone, such as acetylacetonate or dimethylglyoxime, metal salts of $C_1$–$C_6$-carboxylic acids and $C_2$–$C_6$-dicarboxylic acids are preferably used, these also being intended to include unsaturated carboxylic acids and dicarboxylic acids as well as hydroxyl-containing carboxylic and dicarboxylic acids, such as maleic acid, lactic acid and tartaric acid. Nickel and cobalt salts of formic acid, acetic acid, propionic acid, butyric acid, valeric acid, caproic acid, oxalic acid, malonic acid, succinic acid, glutaric acid, adipic acid and maleic acid are particularly preferred, nickel formate, cobalt formate, nickel acetate, cobalt acetate, nickel oxalate and cobalt oxalate being very particularly preferred.

The metal salts of the carboxylic and dicarboxylic acids are either commercially available or can be prepared, for example, according to J. of Phys. Chem. 68.4 (1964), 731–732 or J. Am. Chem. Soc. 81 (1959), 2930–2933.

The preparation of the corresponding catalysts from the metal salts of the carboxylic acids and dicarboxylic acids is described in "Preparation of catalysts V, 1991, Elsevier Science Publishers B. V., Amsterdam, pages 165–174 and Coll. Czech. Chem. Comm. 46 (1981), 1011–1022, or can be carried out similarly to the procedure described there, so that further information in this context is unnecessary.

The thermal decomposition of metal carbonyls can be carried out, for example, by processes according to DRP 511 564 or FP 1,317,934.

The thermal decomposition of metal complexes with diketones is usually carried out similarly to the decomposition of the salts of the carboxylic acids, but in a hydrogen atmosphere.

In general, the thermal decomposition is effected in a temperature range from 150° to 500° C., preferably from 180° to 400° C., particularly preferably from 190° to 350° C., the chosen temperature depending specifically on the starting compound used. Furthermore, the thermal decomposition may be carried out either in an inert atmosphere (nitrogen, argon or helium) or in a reducing atmosphere (hydrogen) a pressure from 1Pa to 10 MPa, preferably from 100 Pa to 1MPa, particularly preferably at atmospheric pressure, in a conventional reaction vessel. For the preparation of supported catalysts, the thermal decomposition is carried out in the presence of the desired carrier or of a precursor of the carrier.

In the thermal decomposition, the metal compounds used are as a rule converted into the corresponding metals or mixtures of the metals with the particular metal oxides, depending on the metal compound used, on the duration of the thermal decomposition, on the chosen temperature and on the composition of the gas phase.

The content of nickel or cobalt in the catalyst depends on whether an unsupported or a supported catalyst is prepared. In the case of supported catalysts, the metal content is usually from 1 to 70, preferably from 10 to 40, % by weight.

In addition to nickel or cobalt, the catalysts may also contain further metals, in particular transition metals and metals of the second to fourth main groups of the Periodic Table of Elements, silver, copper, zinc, magnesium, calcium and iron being particularly preferred. The preparation is carried out as a rule by simultaneous or successive thermal decomposition of the corresponding metal compounds, advantageously a mixture of metal compounds being used, preferably one in which the nonmetal-containing residues are identical. For example, coprecipitated nickel oxide and magnesium oxide can be converted into finely divided nickel or magnesium oxide under an inert atmosphere, such as nitrogen, argon or helium, or a reducing atmosphere containing hydrogen (cf. Pre. of Cat. V, 1991, Elsevier, Amsterdam, pages 165–174 and Coll. Czech. Chem. Comm. 46 (1981), 1011–1022).

In a preferred embodiment, nickel catalysts are obtained by the process from Ind. Eng. Chem. 32, No. 9 (1940) 1193–1199, by heating nickel formate in a high-boiling liquid.

Other nickel and cobalt catalysts can preferably be prepared in the liquid phase similarly to the process from Ind. Eng. Chem. 32 No. 9 (1940) 1193–1199, inert substances which have a high boiling point at atmospheric pressure being used, in particular high-boiling saturated $C_9$–$C_{30}$-hydrocarbons, such as white oils and paraffins, high-boiling $C_nH_{2n+3}$ N-amines (where n is from 7 to 25), high-boiling $C_mH_{2m+4}$ N-diamines (where m is from 5 to 35), such as hexamethylenediamine, polyamines, such as polyethyleneimine, and high-boiling alcohols having the composition $(OH)_pC_7H_{2q+2-p}$, such as octanol, propanediol and glycerol. The advantage of this method is that the nickel or cobalt and, if desired, further metals are coated with the high-boiling substance, which of course can also be a solid at room temperature. Observations to date have shown that this coating prevents the admission of oxygen, so that no passivation of the catalyst takes place, and permits the catalyst to be used in a simple manner.

The starting materials used in the novel process are aliphatic α,ω-dinitriles of the formula I $$NC-(CH_2)_n-CN \qquad I$$

where n is an integer from 1 to 10, in particular 2, 3, 4, 5 or 6. Particularly preferred compounds I are succinonitrile, glutaronitrile, adiponitrile, pimelonitrile and suberonitrile, very particularly preferably adiponitrile.

In the novel process, the dinitriles I described above are partially hydrogenated in the presence of a solvent and, if desired, of a base, such as the hydroxide of an alkali metal, in particular lithium hydroxide, sodium hydroxide or potassium hydroxide, preferably lithium hydroxide and one of the catalysts described above, to give α,ω-aminonitriles of the general formula II $$NC-(CH_2)_n-CH_2-NH_2 \qquad II$$

where n has the abovementioned meaning. Particularly preferred aminonitriles II are those in which n is 2, 3, 4, 5 or 6, in particular 4, ie. 4-aminobutyronitrile, 5-aminopentanenitrile, 6-aminohexanenitrile (6-aminocapronitrile), 7-aminoheptanenitrile and 8-aminooctanenitrile, very particularly preferably 6-aminocapronitrile.

If the reaction is carried out in a suspension, temperatures of from 30° to 150° C., preferably from 50° to 100° C., particularly preferably from 60° to 90° C., are usually chosen; the pressure is chosen in general in the range from 2 to 20, preferably from 3 to 10, particularly preferably from 4 to 8, MPa. The residence times are essentially dependent on the desired yield and selectivity and on the desired conversion; the residence time is usually chosen so that a maximum yield is obtained, for example in the range from 30 minutes to 10 hours, preferably from 1 to 5 hours, when adiponitrile is used.

In a suspension procedure, the solvents used are preferably ammonia, amines, diamines and triamines of 1 to 6 carbon atoms, such as trimethylamine, triethylamine, tripropylamine and tributylamine or alcohols, preferably methanol and ethanol, particularly preferably ammonia. A dinitrile concentration of from 10 to 90, preferably from 30 to 80, particularly preferably from 40 to 70, % by weight, based on the sum of dinitrile and solvent, is advantageously chosen.

The hydrogenation in suspension can be carried out batchwise or, preferably, continuously, as a rule in the liquid phase.

The partial hydrogenation may also be carried out batchwise or continuously in a fixed-bed reactor by the trickle-bed or liquid phase procedure, a temperature of from 20° to 150° C., preferably from 30° to 90° C., and a pressure of, as a rule, from 2 to 30, preferably from 3 to 20, MPa usually being chosen. According to the invention, the partial hydrogenation is carried out in the presence of a solvent, preferably ammonia, an amine, a diamine or a triamine of 1 to 6 carbon atoms, such as trimethylamine, triethylamine, tripropylamine or tributylamine, or an alcohol, preferably methanol or ethanol, particularly preferably ammonia. In a preferred embodiment, an ammonia content of from 1 to 10, preferably from 2 to 6, g per g of adiponitrile is chosen. A catalyst space velocity of from 0.1 to 1.0 kg of adiponitrile per 1 per h is preferably chosen. Here too, the conversion and hence the selectivity can be controlled by changing the residence time.

In the novel process, alpha,omega-aminonitriles are obtained with good selectivities, the catalysts having a substantially longer life than the prior art catalysts. The α,ω-aminonitriles are important starting compounds for the preparation of cyclic lactams, in particular 6-aminocapronitrile for caprolactam.

We claim:

1. In a process for the preparation of aliphatic α,ω-aminonitriles of the formula II $$NC-(CH_2)_n-CH_2-NH_2 \qquad II$$

where n is an integer of from 1 to 10, by the partial hydrogenation of aliphatic α,ω-dinitriles of the formula I $$NC-(CH_2)_n-CN$$

where n has the above meaning, at an elevated temperature and under superatmospheric pressure, in the presence of a solvent and a catalyst the improvement which comprises; carrying out the partial hydrogenation in the presence of a catalyst which is prepared by the thermal decomposition of cobalt or nickel salts of $C_1$–$C_6$-carboxylic acids, $C_2$–$C_6$-dicarboxylic acids and cobalt or nickel complexes with 1,2- and 1,3-diketones at a temperature of about 150° to 500° C. and at a pressure from 1 Pa to 10 MPa.

2. The process of claim 1, wherein the cobalt or nickel salt is selected from the group consisting of nickel formate, cobalt formate, nickel acetate, cobalt acetate, nickel oxalate and cobalt oxalate.

3. The process of claim 2, wherein the thermal decomposition of the cobalt or nickel salt takes place at a temperature of 190° to 350° C. at atmospheric pressure.

4. The process of claim 1, wherein the catalysts contain, as further components, metals selected from the group consisting of silver, copper, zinc, magnesium, calcium and iron.

5. The process of claim 1, wherein the α,ω-dinitrile used is adiponitrile, and 6-aminocapronitrile is obtained.

* * * * *